(12) United States Patent
Pratt

(10) Patent No.: US 7,461,565 B2
(45) Date of Patent: Dec. 9, 2008

(54) CONDITIONING CHAMBER FOR METALLURGICAL SURFACE SCIENCE

(75) Inventor: Allen Pratt, Ottawa (CA)

(73) Assignee: Her Majesty the Queen in right of Canada as represented by the Minister of Natural Resources, Ottawa, Ontario (CA)

( * ) Notice: Subject to any disclaimer, the term of this patent is extended or adjusted under 35 U.S.C. 154(b) by 64 days.

(21) Appl. No.: 11/115,274

(22) Filed: Apr. 27, 2005

(65) Prior Publication Data
US 2005/0193837 A1  Sep. 8, 2005

Related U.S. Application Data

(63) Continuation-in-part of application No. 10/259,747, filed on Sep. 30, 2002.

(51) Int. Cl.
*G01N 1/00* (2006.01)
(52) U.S. Cl. ........................ 73/863; 73/865.8
(58) Field of Classification Search ............... 73/865.8, 73/863, 866; 250/288, 358.1, 359.1, 360.1, 250/491.1
See application file for complete search history.

(56) References Cited

U.S. PATENT DOCUMENTS

| 3,720,829 | A | * | 3/1973 | Palmberg ............... 250/440.11 |
| 4,904,141 | A |   | 2/1990 | Contin |
| 5,033,720 | A |   | 7/1991 | Chen |
| 5,139,383 | A |   | 8/1992 | Polyak et al. |
| 5,200,136 | A |   | 4/1993 | Ramaseder et al. |
| 5,518,593 | A |   | 5/1996 | Hosokawa et al. |
| 5,954,489 | A |   | 9/1999 | Kinoshita |

OTHER PUBLICATIONS

Smart, R. St. C, Minerals Engineering vol. 4 pp. 891-909, 1991.

* cited by examiner

*Primary Examiner*—Robert Raevis

(57) ABSTRACT

The present invention provides a conditioning chamber device for metallurgical samples, adapted to be attached to an instrument having an examination chamber operable in an ultra high vacuum condition, and to be brought to an ultra high vacuum condition while attached to the instrument; and comprises (i) at least one vacuum pump means; (ii) a sample retaining means; (iii) at least one fracturing means adapted to prepare on a sample a surface suitable for metallurgical analysis; (iv) a drying means adapted for slow drying of a sample in an ultra high vacuum condition; and (v) a transporting means to transport the sample after surface preparation through a connecting means into the examination chamber.

9 Claims, 2 Drawing Sheets

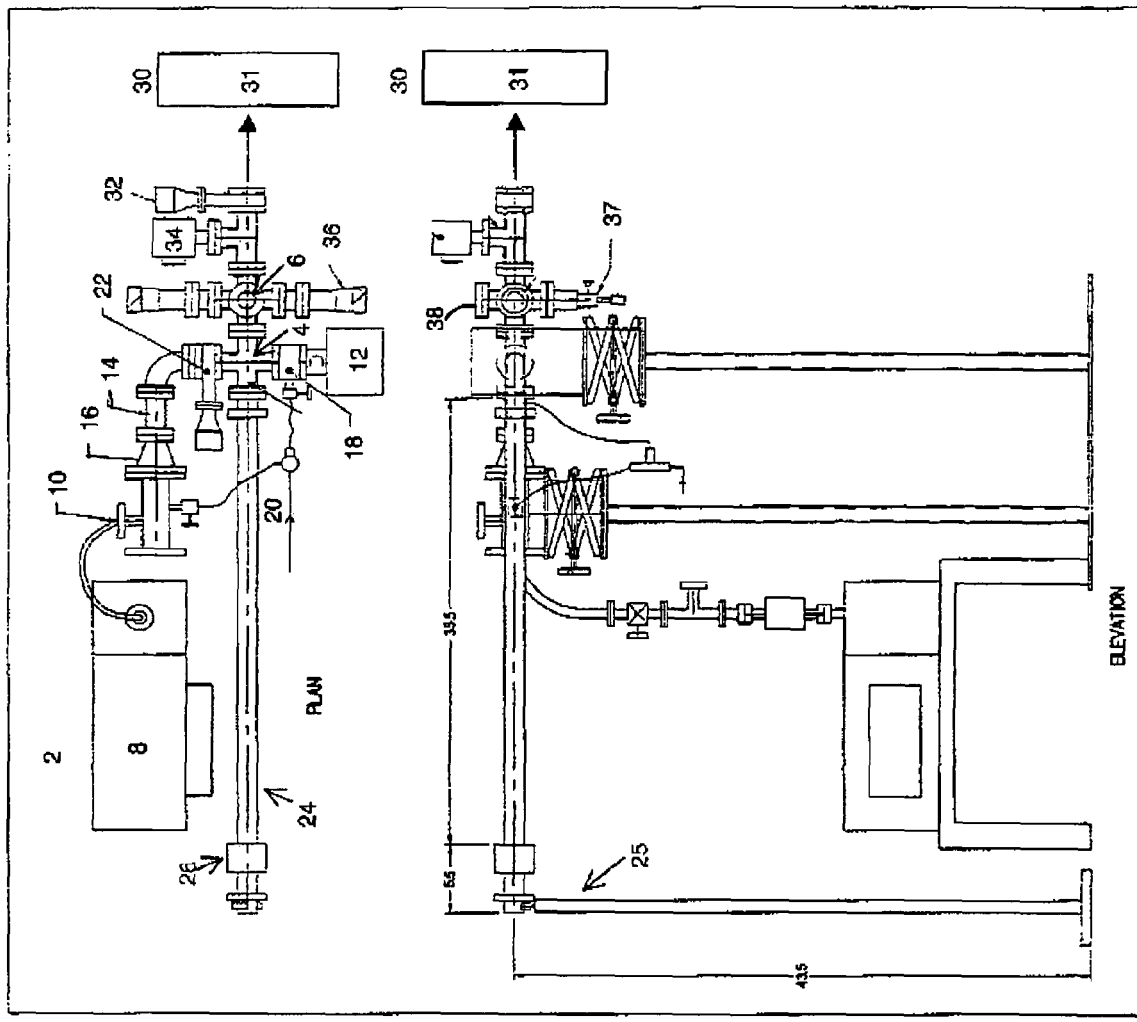

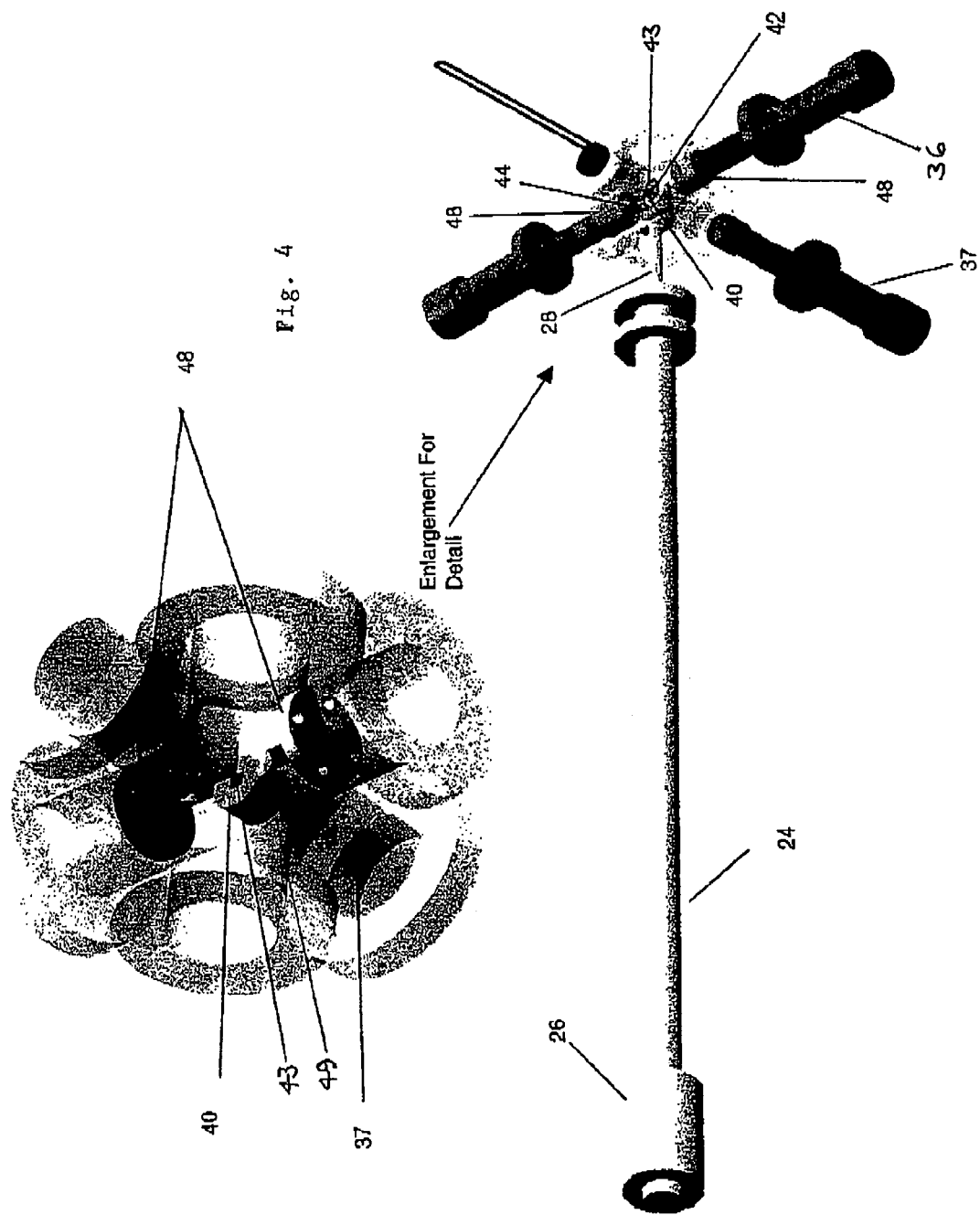

CONDITIONING CHAMBER FOR METALLURGICAL SURFACE SCIENCE

This is a Continuation-in-part of U.S. patent application Ser. No. 10/259,747, filed Sep. 30, 2002.

FIELD OF THE INVENTION

This invention relates to conditioning chambers for preparation of metallurgical samples for examination and analysis.

BACKGROUND OF THE INVENTION

Metallurgical processing for surface science research typically involves the examination of a sample in a vacuum chamber of an examination instrument, generally in an ultra high vacuum (UHV) condition, which can be defined as a pressure which is below $10^{-9}$ Torr. Typically, samples are prepared for such research in separate instruments, before an appropriate sample is introduced to a UHV examination chamber.

Such preparation involves up to two stages, comprising (1) drying or (2) fracturing or both, each of which presents problems.

In the drying stage, metallurgical samples, which are generally wet, can be dried for analysis by various known methods, which include drying in an inert gas environment in a suitable container. Another known method is drying in a forechamber which is available as an attachment to known examination instruments. This method, developed at the Ian Wark Institute in Adelaide, Australia, is described in the text Minerals Engineering, 1991, Smart, R. St. C., vol. 4, pp. 891-909.

There are problems arising from the use of either of these two principal known methods of drying samples for analysis. Firstly, where a sample is dried in an inert atmosphere not directly connected to the examination instrument, there are risks of adverse effects during transport to the instrument, including from air exposure. Secondly, where a sample is dried in a forechamber to the instrument, although the air exposure risk is reduced or removed, there is a risk of adverse effect on the UHV conditions of the examination chamber when the sample is moved into that chamber.

Further, there is the problem that arises from the length of time required for preparation of such samples in the forechamber. Although a typical forechamber is designed to be pumped down to the desired vacuum condition in a relatively short period, of approximately twenty minutes, the process is of necessity substantially longer, often many hours, for proper preparation of metallurgical samples. While such samples are in the forechamber, the examination chamber cannot be accessed for other work, and valuable instrument time is thus lost.

In the second stage, the fracturing of the sample to obtain a suitable surface for analysis, the methods currently in use also raise problems. Typically, these methods involve a high energy impact, for example impact by the use of a hammer and chisel in a UHV chamber, after freezing of the sample to an extremely low temperature, generally below 75 K. However, if this method is used for a brittle material, the entire sample can be destroyed. If instead fracturing is performed in an inert gas in a location which is remote from the examination instrument, there is a serious risk of contamination during transfer to that instrument, the risk being increased by the more reactive nature of the surfaces which have been exposed by fracture. Further limiting factors at this stage include the shape and size of samples.

Typically also, a single chisel is used, which is generally effective in many situations. However, it has been found that for metallurgical samples, greater effectiveness and precision can be achieved, without high impact and without any manifest disadvantages, by the use of a pair of chisels, preferably in opposed directions in relation to each other.

It has been found that a conditioning chamber can be provided which can be attached to, and directly connected with, a UHV examination chamber; and in which a sample can be prepared by drying and fracturing for subsequent transfer into the examination chamber, thereby avoiding the problems associated with the extended drying time which may be required, and with the risks presented by transfer from a remote drying location to the examination chamber.

It has also been found that the use of vacuum pumps of more than one type can improve the attainment of the desired UHV condition. It has further been found that the use of appropriate retaining means within the chamber can enable the use of dual chisels for fracturing, with consequent improved quality and reduced risk of damage to the sample during fracturing. Further, it has been found that the retaining means for the sample within the conditioning chamber can be combined with suitable transporting means to move the prepared sample into the examination chamber of an instrument through a connecting means.

The invention seeks to provide a conditioning chamber which includes an improved environment for drying metallurgical samples for analysis in UHV instruments, and in which the surface preparation by fracturing can also be performed, thus minimizing the risks of contamination from exposure to air or other changed conditions during transfer.

The invention further seeks to provide improved sample retaining and fracturing means which reduce the risk of destruction of or damage to samples during the fracturing process.

SUMMARY OF THE INVENTION

The present invention provides a conditioning chamber device for metallurgical samples, adapted to be attached to an instrument having an examination chamber operable in an ultra high vacuum condition, and to be brought to an ultra high vacuum condition while attached to the instrument; and comprises
 (i) at least one vacuum pump means;
 (ii) a sample retaining means;
 (iii) at least one fracturing means adapted to prepare on a sample a surface suitable for metallurgical analysis;
 (iv) a drying means adapted for slow drying of a sample in an ultra high vacuum condition; and
 (v) a transporting means to transport the sample after surface preparation through a connecting means into the examination chamber.

In the conditioning chamber device of the invention, an enclosed conditioning chamber is provided which is attachable to a commercially available examination instrument having an ultra high vacuum instrument chamber. Within the conditioning chamber, a metallurgical sample can be retained by a suitable means, while the conditioning chamber is gradually reduced to the desired vacuum condition, by the use of at least one vacuum pump. Preferably more than one type of pump is used, and more preferably the pumping is performed in sequence by a rotary vane pump, a turbomolecular pump and a triode ion pump.

Preferably, the retaining means is a gripper which is designed to retain a standard sample platen holder in the desired position throughout the conditioning process. To facilitate movement of the sample after the conditioning process is complete, a transporter rod is provided, which is securely attached, and preferably permanently affixed, to the gripper or other retaining means. The transporter rod is contained within a tube, attached to the outside of the housing of the conditioning chamber. A magnetic sleeve surrounding the tube along part of its length is magnetically coupled with the transporter rod, such that movement of the sleeve will direct the rod along the axial direction of the tube. Such movement of the rod thus effects the desired movement of the sample retaining means, and thus the sample on the platen, in particular for transporting the sample out of the conditioning chamber to the examination chamber of an examination instrument, as described below.

After the conditioning chamber has been reduced to the desired vacuum condition, and the sample has been dried to the required state, it can be fractured by chisels, preferably a pair of chisels operating in opposed directions in relation to each other.

The conditioning chamber device is attachable to a commercially available examination instrument having an ultra high vacuum examination chamber, the attachment being in such manner as to enable the device to operate without interference with the instrument itself or its operation, or with a forechamber or other attachments to the examination instrument. The device is provided with a connecting means through which, after completion of the conditioning process, and fracturing to provide a suitable surface for analysis, the prepared sample can be transferred into the examination chamber without loss of vacuum or any risk of contamination from contact with outside air. Once the sample is in the examination chamber of the instrument, it can be subjected to the desired analysis.

BRIEF DESCRIPTION OF THE DRAWINGS

The invention will now be described by way of reference to the drawings, in which FIG. 1 is a plan view of an embodiment of the invention;

FIG. 2 is a side elevation view of the embodiment shown in FIG. 1;

FIG. 3 is an isometric view of the retaining, fracturing and transporting means of the embodiment shown in FIG. 1; and FIG. 4 is an enlarged view of the retaining and fracturing means of the embodiment shown in FIG. 3.

DETAILED DESCRIPTION OF THE PREFERRED EMBODIMENT

Referring to FIG. 1, a conditioning chamber device 2 comprises a housing 4, enclosing a chamber 6 which can be brought to an ultra high vacuum (UHV) condition, at or below $10^{-9}$ Torr. To achieve this condition, a rotary vane pump 8, a turbomolecular pump 10 and a triode ion pump 12 are provided which are operable in sequence. The pumps 8, 10 and 12 are connected to the chamber 6 by suitable known linkage components (not specifically identified). As shown in FIG. 1, the first two pumps 8 and 10 are located so as to be connected to the chamber 6 by a first gate valve 22, and the third pump 12 is located so as to be connected to the chamber 6 at a second location, shown in FIG. 1 as adjacent to an up-to-air valve 18, and on the opposite side of the chamber 6 from the connection of the first two pumps 8 and 10. However, any suitable arrangement of the pumps 8, 10 and 12 can be selected such that the pumps can be operated and controlled effectively. Inert gas connection lines 20 for venting the chamber 6 are provided.

Attached to the housing 4, at a suitable location selected to avoid interference with the connection of the pumps 8, 10 and 12, is a cylindrical tube 24, supported at a free end 25 (shown in FIG. 2). A cylindrical magnetic sleeve 26 surrounds the tube 24 along part of its length, and is movable along the length of the tube 24 such that the magnetic force can move a transporter rod 28, (shown in FIG. 3) which is magnetically coupled with the magnetic sleeve 26, and contained within the tube 24, the direction of movement being along the axial direction of the tube 24.

The chamber 6, at a location opposed to the connection of the tube 24 with the chamber 6, is provided with connection means for attachment to an examination instrument 30. The chamber 6 is provided with a second gate valve 32, having suitable controls including vacuum gauge 34. Adjacent to the second gate valve 32, the conditioning chamber device 2 can be attached by suitable further connection means (not shown) to the examination instrument 30, such that in an open position the interior of the chamber 6 can be directly connected to the examination chamber 31 of the examination instrument 30.

Horizontal linear motion feeders 36 are provided at each side of the housing 4 to effect horizontal movement within the chamber 6, and vertical linear motion feeder 37 (shown in FIG. 2) is provided below the housing 4 to effect vertical movement within the chamber 6.

Referring to FIGS. 1 and 2, a sealable access flange 38 is provided at the upper region of the housing 4 to enable the placement of a sample (not shown in FIGS. 1 and 2) within the chamber 6.

Referring to FIGS. 3 and 4, a sample 42 is supported by a sample platen 43 on pedestal 40, the vertical position of the pedestal 40 being regulated by vertical linear motion feeder 37. The pedestal 40 is retained in a desired position by a retaining means, such as gripper 44, which is securely or preferably permanently fixed to the transporter rod 28, within tube 24, and controlled by magnetic sleeve 26. A sample 42 can be placed securely on the sample platen 43. Located on each side of the sample platen 40, and regulated by horizontal linear motion feeders 36, are chisels 48, which can be brought into contact with the sample 42.

In the operation of the conditioning chamber device 2, the sample 42 on sample platen 43 is introduced to the chamber through access flange 38, on pedestal 40, which is secured by suitable known means to the pedestal 40 which is retained in position by the gripper 44. As soon as the sample 42 is secured in the desired position, the access flange 38 is secured and capped. At this point, the second gate valve 32 is in a closed position. The chamber 6 can thus be brought to the desired UHV condition by means of the three pumps 8, 10 and 12 in sequence. The rotary vane pump 8 can be used to reduce the pressure to $10^{-2}$ Torr, and the turbomolecular pump 10 can be used to reduce the pressure further to $10^{-7}$ Torr. To complete the process, the triode ion pump 12 is used to reduce the pressure to the desired level below $10^{-7}$ Torr, which will correspond to the level at which the examination chamber 31 will have been prepared prior to movement of the sample 42 into the examination chamber 31.

The timing of the pressure reduction process can be selected as desired, according to the properties of the sample. At this stage, the conditioning chamber device 2 is already attached to the examination instrument 30, but the chamber 6 is not internally connected with the examination chamber 31. The examination chamber 31 can thus be used for any other purposes during this time period, avoiding any unnecessary down-time for the examination chamber 31 during the sample conditioning process.

As can be more clearly seen in FIG. 4, when fracturing is required, the sample 42 can be fractured using the chisels 48, having cutting edges 49. The chisels, or at least the edges, are preferably made of tempered steel. Using external controls (not shown) operating on the respective elements indicated in FIG. 4, the chisels 48 are brought to the sample 42, and a suitable surface can be prepared to allow for the desired analysis.

When the fracturing of the sample 42 is complete, the chamber 6 can be internally connected to the examination chamber 31, by the opening of the second gate valve 32. The examination chamber will have been prepared to the desired UHV condition. By movement of the magnetic sleeve 26 along the tube 24, the magnetically coupled transporter rod 28 is moved in a direction along the axis of the tube 24. Thus, the sample 42 on the sample platen 43 on pedestal 40, which is still retained by the gripper 44, can be moved from the chamber 6 to the examination chamber 31, for the desired analysis process.

It can thus readily be seen that throughout the conditioning and fracturing process, there is no movement of the sample 42 itself which could result in damage, and no exposure to the risk of contamination during a transport process from a remote location to the examination chamber 31.

Each of the components of the conditioning chamber device 2 of the invention can be constructed of any suitable materials which are, or can be determined to be, compatible for operation within UHV conditions.

I claim:

1. A conditioning chamber device for metallurgical samples, adapted to be attachable to an instrument having an examination chamber operable in an ultra high vacuum condition, and to be brought to an ultra high vacuum condition while attached to the instrument; the conditioning chamber comprising
    (i) vacuum pump means, provided to the conditioning chamber and comprising a rotary vane pump, a turbomolecular pump and a triode ion pump;
    (ii) a sample retaining means;
    (iii) at least one fracturing means adapted to prepare on a sample a surface suitable for metallurgical analysis;
    (iv) a drying means adapted for slow drying of a sample in an ultra high vacuum condition; and
    (v) a transporting means to transport the sample after surface preparation through a connecting means into the examination chamber.

2. A conditioning chamber device as claimed in claim 1 wherein the fracturing means comprises a pair of chisels operable from substantially opposed directions in relation to each other.

3. A conditioning chamber device as claimed in claim 2 wherein each of the chisels has a cutting edge of tempered steel.

4. A method of conditioning a metallurgical sample for surface analysis by the steps of
    (i) securing the sample by a sample retaining means within a conditioning chamber capable of being reduced to an ultra high vacuum condition, and attachable to an instrument having an examination chamber operable in an ultra high vacuum condition;
    (ii) reducing the conditioning chamber to an ultra high vacuum condition by a vacuum pump means comprising a rotary vane pump, a turbomolecular pump and a triode ion pump;
    (iii) drying the sample;
    (iv) fracturing the sample by a fracturing means to prepare a surface suitable for metallurgical analysis; and
    (v) subsequently transporting the sample by a transportation means from the conditioning chamber into the examination chamber.

5. A method as claimed in claim 4, wherein the fracturing means comprises a pair of chisels operable from substantially opposed directions in relation to each other.

6. A method as claimed in claim 4, wherein the transporting means comprises a transporter rod attached to the sample retaining means, wherein movement of the transporter rod is regulated by an external control means.

7. A method as claimed in claim 6, wherein the sample retaining means comprises a gripping means permanently attached to the transporter rod.

8. A method as claimed in claim 6, wherein the external control means comprises magnetic coupling.

9. A method as claimed in claim 8, wherein the external control means comprises magnetic coupling.

* * * * *